United States Patent [19]
Hase

[11] Patent Number: 5,841,022
[45] Date of Patent: Nov. 24, 1998

[54] GAS ANALYZER AND GAS ANALYSIS METHOD

[75] Inventor: Ushio Hase, Tokyo, Japan

[73] Assignee: NEC Corporation, Tokyo, Japan

[21] Appl. No.: 915,117

[22] Filed: Aug. 20, 1997

[30] Foreign Application Priority Data

Sep. 12, 1996 [JP] Japan .................................... 8-241943

[51] Int. Cl.⁶ .................................................. G01N 30/20
[52] U.S. Cl. .................... 73/23.22; 73/23.41; 73/864.83; 422/88; 422/93
[58] Field of Search .............................. 73/23.22, 23.41, 73/23.42, 864.83, 864.84; 422/88–89, 93

[56] References Cited

U.S. PATENT DOCUMENTS

| | | | |
|---|---|---|---|
| 3,926,561 | 12/1975 | Lucero | 23/232 B |
| 3,976,450 | 8/1976 | Marcote et al. | 55/158 |
| 4,271,695 | 6/1981 | Sisti et al. | 73/23.1 |
| 4,359,891 | 11/1982 | Ahlstrom, Jr. et al. | 73/23.1 |
| 4,472,354 | 9/1984 | Passel et al. | 422/62 |
| 5,073,502 | 12/1991 | Steele, Jr. | 436/125 |
| 5,152,176 | 10/1992 | Bryselbout et al. | 73/23.41 |
| 5,352,272 | 10/1994 | Moll et al. | 96/9 |
| 5,591,406 | 1/1997 | Hirai et al. | 422/80 |
| 5,714,676 | 2/1998 | Hase | 73/23.41 |

FOREIGN PATENT DOCUMENTS

| | | |
|---|---|---|
| 8054380A | 2/1996 | Japan . |
| 8233706 | 9/1996 | Japan . |
| 0371508 | 2/1973 | U.S.S.R. . |
| 1734005 | 5/1992 | U.S.S.R. . |

OTHER PUBLICATIONS

Ushio Hase, "Automatic Monitor for Ammonia in Clean Room Air", *The Fifth International Symposium on Semiconductor Manufacturing*, pp. 151–154.

*Primary Examiner*—Hezron E. Williams
*Assistant Examiner*—J. David Wiggins
*Attorney, Agent, or Firm*—Sughrue, Mion, Zinn, Macpeak & Seas, PLLC

[57] ABSTRACT

The present invention provides a gas analyzer used for contamination control of a clean environment by collecting samples from a plurality of measurement points while switching these points and continuously monitoring the volatile components present in the air of the environment, which analyzer requires no increase in number of parts and can give good response in a short period of measurement; and a gas analysis method using the gas analyzer.

The gas analyzer of the present invention has two gas sampling units. Each of solution-feeding pumps 3, 15 is actuated for a different diffusion scrubber. The diffusion scrubber connected to the solution-feeding pump 15 is put in a measurement state; and the to-be-analyzed gas components absorbed by the absorbing solution in the diffusion scrubber are captured by a concentration column 14 and are analyzed by an ion chromatograph 30. During this period, a preliminary operation is conducted, in parallel, in the other diffusion scrubber connected to the solution-feeding pump 3. Thus, the adverse effect of the previous analysis by memory effect is prevented; response is improved; and the period of measurement is shortened.

7 Claims, 8 Drawing Sheets

GAS ANALYZER AND GAS ANALYSIS METHOD

BACKGROUND OF THE INVENTION

1. Field of the Invention

The present invention relates to a gas analyzer used for contamination control of a clean environment by collecting samples from a plurality of measurement points while switching these points and continuously monitoring the volatile components present in the air of the environment; and a gas analysis method using the gas analyzer.

2. Description of the Related Art

In recent years, there were developed gas analyzers using, for sampling of a sample gas, a diffusion scrubber which absorbs the water-soluble gas components present in the sample gas, with an absorbing solution. Such gas analyzers are known in, for example, Analytical Chemistry, Vol. 61, No. 1, Jan. 1989 or Japanese Patent Application Laid-Open JP-A 8-54380. The gas analysis method using such a gas analyzer, as compared with a gas analysis method for ammonia or acidic gas components in gas by impinger sampling which has long been used, requires a short sampling time of $\frac{1}{5}$ to $\frac{1}{10}$, enables on-site automatic measurement in a measurement period of less than one hour and, therefore, is useful for gas monitoring conducted, for example, when the concentration of ammonia or acidic gas components in production site environment must be strictly controlled. A gas analyzer using, in combination, a diffusion scrubber-based gas sampling unit and an ion chromatograph, disclosed in Japanese Patent Application Laid-Open JP-A 8-54380, is shown in FIG. 8. In the gas analyzer of FIG. 8, a diffusion scrubber body 10 is tube-shaped and comprises an outer tube 5 and an inner tube 4 provided inside the outer tube and consisting of a gas-permeable membrane tube. An absorbing solution enters the diffusion scrubber through an inlet 6 and leaves from an outlet 7. While the absorbing solution is continuously passed through the gap between the outer tube and the inner tube, a sample gas is sucked by a sampling pump and continuously passed inside the inner tube, whereby the to-be-analyzed gas components in the sample gas are absorbed by the absorbing solution in the diffusion scrubber. The absorbing solution which has absorbed the to-be-analyzed gas components, is passed through a concentration column 14 to allow the column to capture and concentrate the components. The analytical steps using the gas analyzer comprises the following steps in the following order:

(1) a preliminary step of bringing the to-be-analyzed gas components in the sample gas to an equilibrium with the to-be-analyzed gas components in the absorbing solution, (2) a rinsing step of, after the preliminary step (1), removing the eluting solution remaining in the concentration column, with pure water, (3) a sampling step of, after the rinsing step (2), introducing the absorbing solution which has absorbed the to-be-analyzed gas components, from the diffusion scrubber into the concentration column and concentrating the components, and (4) an analysis step of, after the sampling step (3), eluting the to-be-analyzed gas components captured by the concentration column and subjecting the resulting eluate to ion chromatography. When there is a sudden change in the concentration of the to-be-analyzed gas components in the sample gas, the analysis result right after the concentration change becomes inaccurate according to the memory effect of the diffusion scrubber, although the inaccuracy varies depending upon the properties of the diffusion scrubber used, particularly the properties of the gas-permeable membrane tube. In the gas analyzer disclosed in Japanese Patent Application Laid-Open JP-A 8-54380, the memory effect (the adverse effect of previous analysis) is minimized by conducting the preliminary step (1) prior to the sampling step (3).

In analyzing particular components in a gas by switching the points of gas sampling (the points of measurement), the switching gives rise to change in concentration of the particular components. Therefore, it is necessary to conduct a preliminary operation for a sufficient length of time or to conduct several times of measurements consecutively and use the final measurement data as a true measurement data. Therefore, when measurement is conducted by switching the points of sampling, about one hour is required for the measurement of one sampling point although only about 20 minutes is required for the measurement of one sampling point when the measurement is made plurality of times consecutively. In Japanese Patent Application Laid-Open JP-A 8-54380 is also disclosed a gas analyzer used for gas analysis by switching of a plurality of sampling points, which comprises two lines except for the ion chromatograph. In this gas analyzer, however, a larger number of parts are needed; the total size is large; and the production cost is high.

SUMMARY OF THE INVENTION

The objects of the present invention are to provide a gas analyzer used for contamination control of a clean environment by collecting samples from a plurality of measurement points while switching these points and continuously monitoring the volatile components present in the air of the environment, which analyzer requires no increase in number of parts and can give good response in a short period of measurement; and a gas analysis method using the gas analyzer.

The above objects of the present invention have been achieved by employing various means to increase the operational efficiency of gas analyzer and shorten the period of measurement by gas analyzer.

According to the present invention, the concentration of gas contaminants present in a clean environment (e.g. clean room) of production site can be controlled quickly and automatically. Therefore, the present invention is suitable for the cleanness control of an environment of semiconductor production process, making possible an increase in device reliability and yield.

The present invention provides a gas analyzer used for analysis of the to-be-analyzed gas components contained in a sample gas, by absorption into an absorbing solution, which gas analyzer comprises:

two gas sampling units each comprising a tube-shaped diffusion scrubber and a sampling pump, each diffusion scrubber comprising an outer tube and an inner tube provided inside the outer tube and consisting of a gas-permeable membrane tube capable of passing therethrough only part of a sample gas, including to-be-analyzed gas components, the outer tube and the inner tube being fixed by a pair of joints at their two ends, the diffusion scrubber further comprising, at each end, a port communicating with the inner tube and a port communicating with the gap between the outer tube and the inner tube, either one of the inner tube inside and the gap between the outer tube and the inner tube being used as a passage for absorbing solution and the other being used as a passage for sample gas, and each sampling pump being connected to the passage for sample gas, of the diffusion scrubber and used for taking the sample gas into the diffusion scrubber, a solution-feeding pump for feeding an absorbing solution into the diffusion scrubber of one gas sampling unit, a solution-feeding pump for feeding the absorbing solution into the diffusion scrubber of the other gas sampling unit and introducing the solution leaving the diffusion scrubber, into a concentration column packed with an adsorbent capable of concentrating the to-be-analyzed gas components dissolved in the solution, a passage-switching valve or device for switching the gas sampling unit connecting to the former solution-feeding pump and the gas sampling unit connecting to the latter solution-feeding pump, to each other, a detecting unit for detecting the to-be-analyzed gas components captured by the concentration column, and a passage-switching valve or device for switching, to each other, a passage for introducing the solution leaving the diffusion scrubber, into the concentration column for capturing and concentration of the to-be-analyzed gas components and a passage for introducing the to-be-analyzed gas components captured and concentrated by the concentration column, into the detecting unit.

In the above gas analyzer, a passage-switching valve for switching gas-sampling points may be provided upstream of the gas inlet of each gas sampling unit.

In the above gas analyzer, the gas-permeable membrane tube preferably has a porosity of 40–80%, a membrane thickness of 0.1–0.5 mm and a water entry pressure of 0.2 kgf/cm$^2$ or more.

The present invention also provides a gas analysis method using the above gas analyzer, which comprises the following steps a, b and c in this order:

a step a of feeding, into one of the gas sampling units, an absorbing solution by the use of one solution-feeding pump and, simultaneously therewith, a sample gas containing to-be-analyzed gas components, to bring the to-be-analyzed gas components in the sample gas to an equilibrium with the to-be-analyzed gas components in the absorbing solution, a step b of, after the step a, introducing the absorbing solution from the diffusion scrubber of the gas sampling unit into the concentration column by the use of another solution-feeding pump, and a step c of, after the step b, eluting the to-be-analyzed gas components captured by the concentration column and analyzing them by the use of the detecting unit, in which method while the step b and the step c are conducted for the sample gas taken into one gas sampling unit, the step a is conducted for the gas sample taken into the other gas sampling unit.

The present invention also provides a gas analyzer for carrying out the above gas analysis method, which has a control unit capable of calculating the times for the steps a to c based on the values inputted as the minimum required times for the steps a to c and also on the value inputted as a desired period of measurement.

In the above gas analysis method, it is preferable that as soon as the step c is completed for the sample gas taken into one gas sampling unit, the step b is started for the sample gas taken into the other gas sampling unit.

Also in the above gas analysis method, it is preferable that as soon as the step b is completed for the sample gas taken into one gas sampling unit, the step a for next cycle is started in the gas sampling unit and this step a is completed as soon as the step c is completed for the gas sample taken into the other gas sampling unit.

DETAILED DESCRIPTION OF THE PREFERRED EMBODIMENTS

Figure 1:
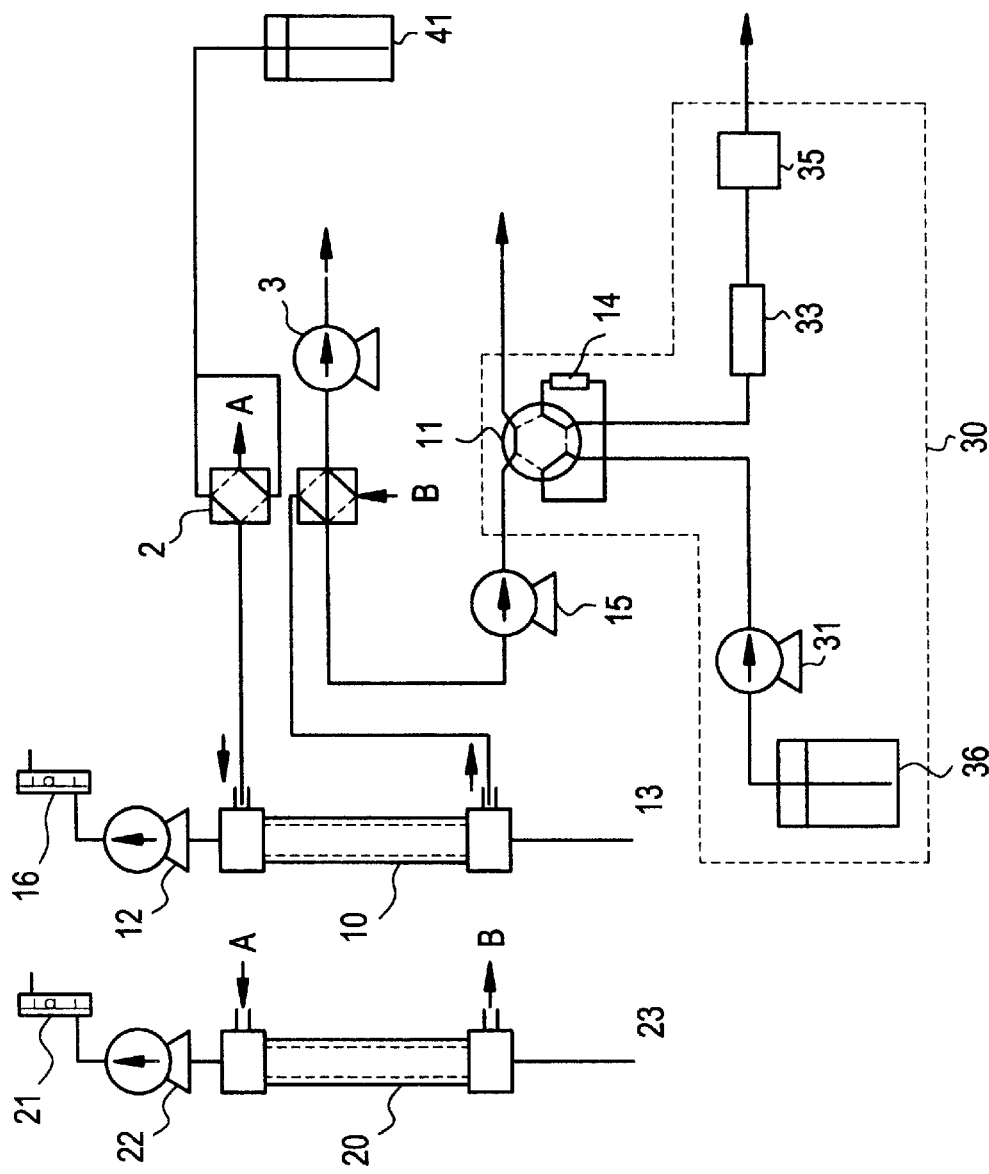
FIG. 1 outlines the total constitution of one embodiment of the present gas analyzer.
Figure 2:
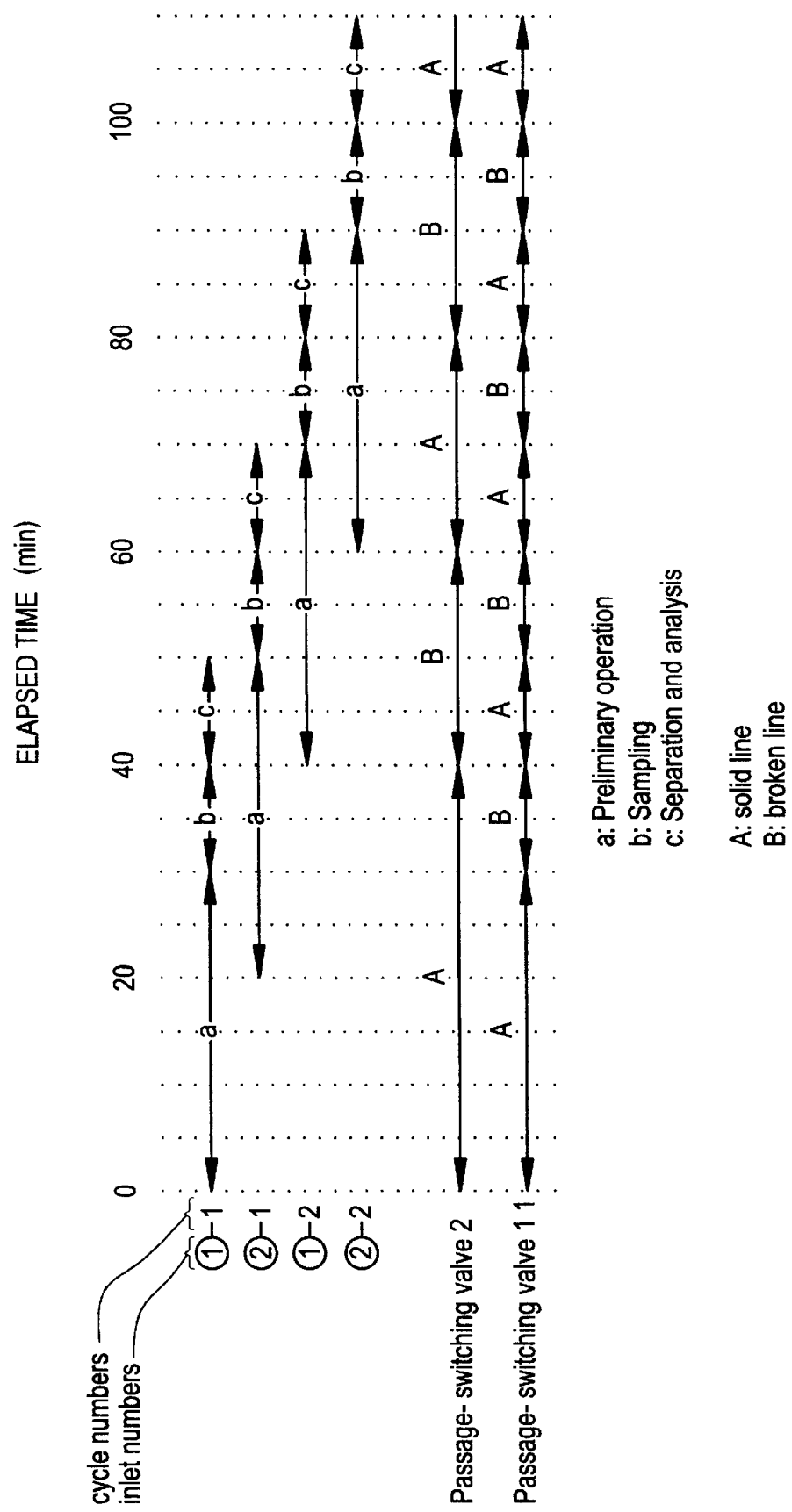
FIG. 2 shows an operational sequence of analytical steps, employed when using the gas analyzer of FIG. 1.
Figure 3:
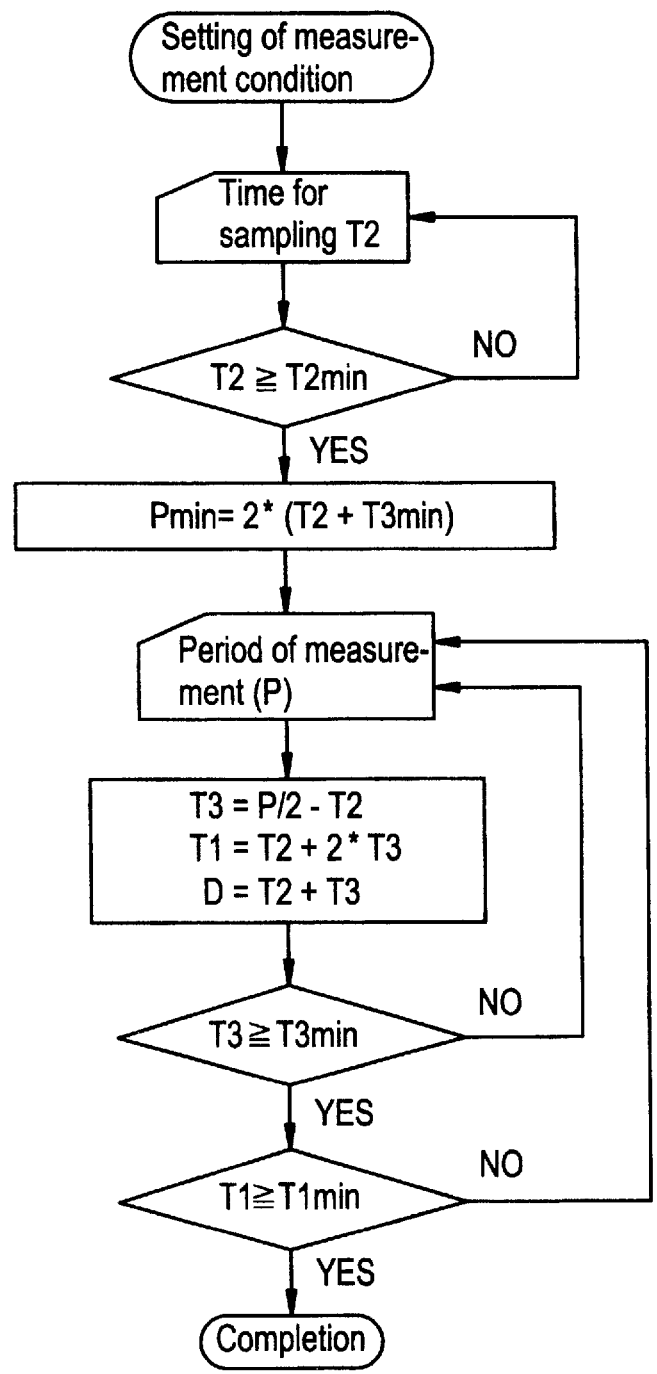
FIG. 3 is a flow chart showing a procedure for setting the measurement conditions used in conducting the operational sequence of FIG. 2.
Figure 4:
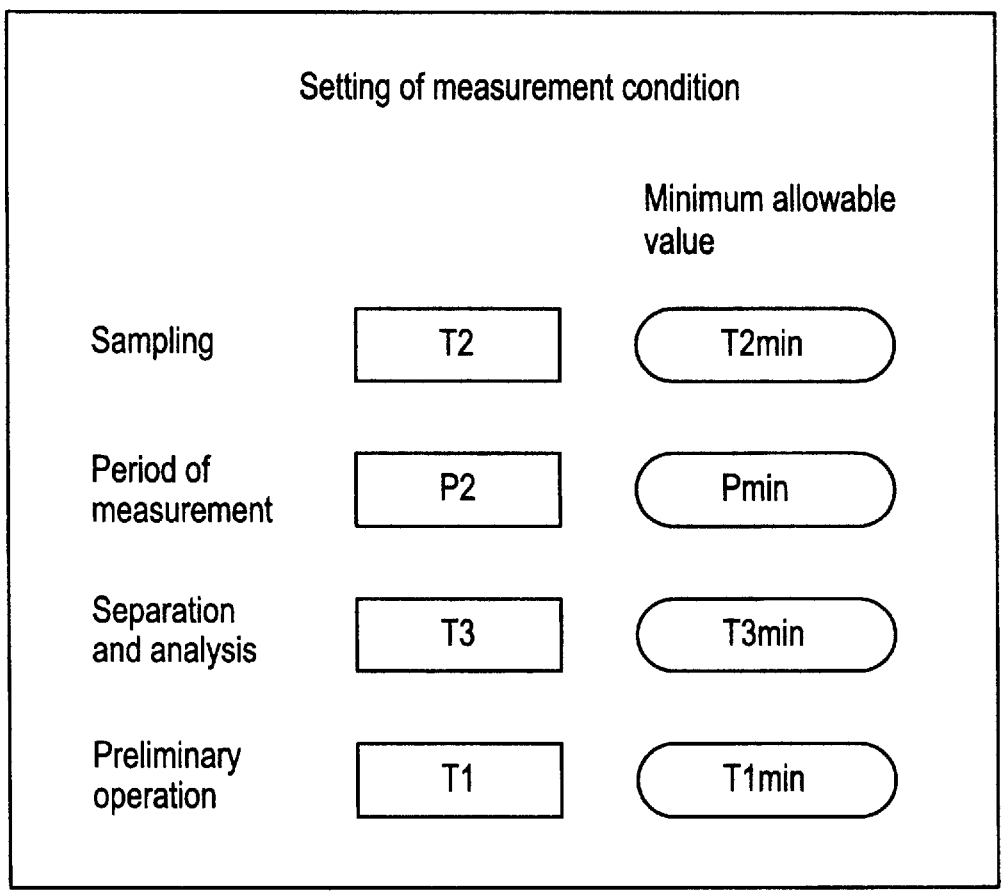
FIG. 4 is a schematic drawing of the screen (used for setting measurement conditions) of the control unit of the gas analyzer of FIG. 1 (the control unit is not shown in FIG. 1).

The first embodiment of the present invention is described with reference to part of the accompanying drawings. FIG. 1 outlines the total constitution of the first embodiment of the present gas analyzer; FIG. 2 shows an operational sequence of analytical steps, employed when using the gas analyzer of FIG. 1; FIG. 3 is a flow chart showing a procedure for setting the measurement conditions used in conducting the operational sequence of FIG. 2; and FIG. 4 is a schematic drawing of the screen (used for setting measurement conditions) of the control unit of the gas analyzer of FIG. 1 (the control unit is not shown in FIG. 1).

In FIG. 1, A and B of a diffusion scrubber body 20 are connected to A and B of a passage-switching valve 2, respectively. In FIG. 2, ①-1 and ①-2 are, respectively, the first and second measurements of a gas taken into from a gas inlet 13; and ②-1 and ②-2 are, respectively, the first and second measurements of a gas taken into from a gas inlet 23. In each measurement, a, b and c refer to a preliminary operation step, a sampling step and a separation and analysis step, respectively. In FIG. 2, the times for preliminary operation are all the same; however, only the time for preliminary operation for ②-1 may be longer. For example, the step a of ①-1 and the step a of ②-1 may be started at the same time.

In FIG. 2, "solid line" and "broken line" of each of the passage-switching valves 2 and 11 correspond to the switching condition of each valve in FIG. 1. The absorbing solution fed by a solution-feeding pump 15 passes through a diffusion scrubber body 10 when the passage-switching valve 2 is in a solid line condition, and passes through the diffusion scrubber body 20 when the passage-switching valve 2 is in a broken line condition. The absorbing solution fed by a solution-feeding pump 3 passes through another diffusion scrubber which is different from the diffusion scrubber through which the absorbing solution fed by the solution-feeding pump 15 passes. When the passage-switching valve 11 is in a broken line condition, the solution from the diffusion scrubber is introduced into a concentration column 14, and the to-be-analyzed gas components in the solution is captured by the column 14. When the passage-switching valve 11 is in a solid line condition, preliminary operation and separation/analysis are conducted. That is, in one passage, the to-be-analyzed gas components captured by the concentration column 14 are eluted by an eluting solution sent from a storage tank 36 and fed into a separation column 33. At that time, the other passage is used for preliminary operation. From the start of the preliminary operation of first measurement, an absorbing solution and a sample gas pass through both of the diffusion scrubbers 10 and 20 continuously, and the diffusion scrubber not set for sampling is always used for preliminary operation.

In FIG. 1, each gas inlet of the diffusion scrubber bodies 10 and 20 are provided below the bodies, but the positions of the gas inlets and the diffusion scrubber bodies are not restricted to those shown in FIG. 1. In order for the absorbing solution passage of diffusion scrubber to be always filled with an absorbing solution, it is desirable that the diffusion scrubber bodies be provided vertically with gas inlets provided above the bodies.

The gas-permeable membrane tube constituting each of the diffusion scrubber bodies 10 and 20 preferably has a porosity of 40–80%, a membrane thickness of 0.1–0.5 mm and a water entry pressure of 0.2 kgf/cm$^2$ or more (the water entry pressure is a maximum pressure at which no water permeates a membrane when the membrane is placed between water and a gas and a pressure is applied to the water side). Since a smaller membrane thickness gives a smaller memory effect and a larger porosity gives a higher absorption efficiency, the membrane thickness and the membrane porosity are more preferably 0.1–0.3 mm and 50–80%, respectively.

A time table for individual analytical steps is shown in FIG. 2. The time table for individual analytical steps is not restricted thereto and may be any unless the sampling and separation/analysis for one sampling point and those for other sampling point are conducted simultaneously. When the time table is set so as to satisfy the following condition:

(period of measurement)=2*(time for sampling+time for separation and analysis)

the above requirement can be met and the most efficient operation of ion chromatograph can be achieved. In order to conduct continuous automatic operation, it is further necessary that the time table is set so as to satisfy the following condition:

(time for preliminary operation)≥(time for sampling+time for separation and analysis)

and further so as to allow the preliminary operation to start after the start of the separation and analysis of the prior measurement in the same diffusion scrubber. In using the gas analyzer of FIG. 1, the time table for individual analytical steps is set in accordance with the flow chart of FIG. 3. Minimum allowable values other than minimum allowable value for period of measurement (Pmin) are displayed on a screen (not shown in FIG. 1) for setting of measurement conditions, by inputting them beforehand. An operator inputs, into a T2 space of FIG. 4, a time for sampling (T2) by taking into consideration the concentration of the to-be-analyzed-components at sampling point and the minimum allowable value for sampling (T2min). When a T2 value larger than T2min is inputted, the minimum allowable value for period of measurement (Pmin) calculated from the T2 value and T3min value is displayed at the space for Pmin, of the screen for setting of measurement conditions. The operator inputs a period of measurement (P) by taking the Pmin into consideration; then, a time for preliminary operation (T1), a time for separation and analysis (T3) and a delay time (D) are calculated. Incidentally, the delay time (D) is a difference in analysis time between when using one gas sampling unit and when using the other second gas sampling unit; for example, in FIG. 2, the difference in starting time of step a between ①-2 and ②-2. When T3 and T1 are below the respective minimum allowable values, reinputting of P is required. When an operation of gas analysis is conducted under the thus-determined measurement conditions, the ion chromatograph routinely repeats, after 30 minutes from the start of the operation, sampling and separation/analysis such as shown in FIG. 2, whereby an efficient measurement can be made.

EXAMPLE 1

The first example of the present invention is described in detail with reference to part of the accompanying drawings. Description is made on a gas analyzer of FIG. 1 on a case of analyzing ammonia in a gas using, as the detecting unit of the analyzer, an ion chromatograph 30 (DX 100, a product of Dionex Corporation) comprising a separation column 33 (Ion Pac CS 12, a product of Dionex Corporation), a concentration column 14 (Ion Pac CG 12, a product of Dionex Corporation), a conductivity detector 35 and a suppressor (CSRS-I, a product of Dionex Corporation) (not shown) provided between the separation column 33 and the conductivity detector 35. Ultrapure water as absorbing solution was placed in a storage tank 41, and a 20 mM methylsulfonic acid solution as eluting solution was placed in a storage tank 36. As each of diffusion scrubber bodies 10 and 20, there was used one constituted by (1) an inner tube consisting of a fluororesin-made gas-permeable membrane tube (Poreflon tube, a product of Sumitomo Electric Industries, Ltd.) of 0.3 mm in thickness and 2 mm in inner diameter and (2) an outer tube consisting of a fluororesin-made tube of 10 mm in inner diameter and 12 mm in outer diameter. As a solution-feeding pump 15, there was used a pump having a discharging pressure capable of easily introducing the absorbing solution into the concentration column 14. When the above concentration column (Ion Pac CG 12, a product of Ionex Corporation) is used, the discharging pressure is required to be 30 kgf/cm$^2$ or more and is desirably 50 kgf/cm$^2$ or more. A solution-feeding pump 3 can have a discharging pressure of several kgf/cm$^2$ and can be an inexpensive pump as compared with the pump 15. The flow rate of the solution-feeding pump 36 was set at 1.0 ml/min, and the flow rate of the solution-feeding pump 3 and 15 was set at 2.0 ml/min. By considering the absorbability in diffusion scrubber, the flow rates of sampling pumps 12 and 22 were each set at 0.5 l/min. When the ion chromatograph 30 is actuated under the above conditions, ammonia is eluted in about 4.5 minutes but, in order to elute alkaline earth metal components completely, about 9 minutes are required for separation and analysis. Therefore, the minimum allowable time for separation and analysis (T3min) was set at 10 minutes. The minimum allowable time for preliminary operation (T1min) was set at 20 minutes by considering the memory effect of diffusion scrubber. Since the above ion chromatograph can safely determine at least about 0.1 ng of ammonia, the time for sampling (T2) was set at 10 minutes in the operational sequence of analytical steps, of FIG. 2. T2 was inputted according to the flow chart of FIG. 3; then, the minimum allowable time for period of measurement (Pmin) was calculated to be 40 minutes and displayed. Next, this Pmin value was inputted as the period of measurement (P); then, the time for preliminary operation (T1) became 30 minutes, the time for separation and analysis (T3) became 10 minutes, and the delay time (D) became 20 minutes, as shown in FIG. 2. Using these set values, measurement was conducted, whereby the first analytical data for two sampling points were obtained after 50 minutes and 70 minutes from the start of measurement and, after that, analytical data were obtained every 40 minutes.

EXAMPLE 2

Figure 5:
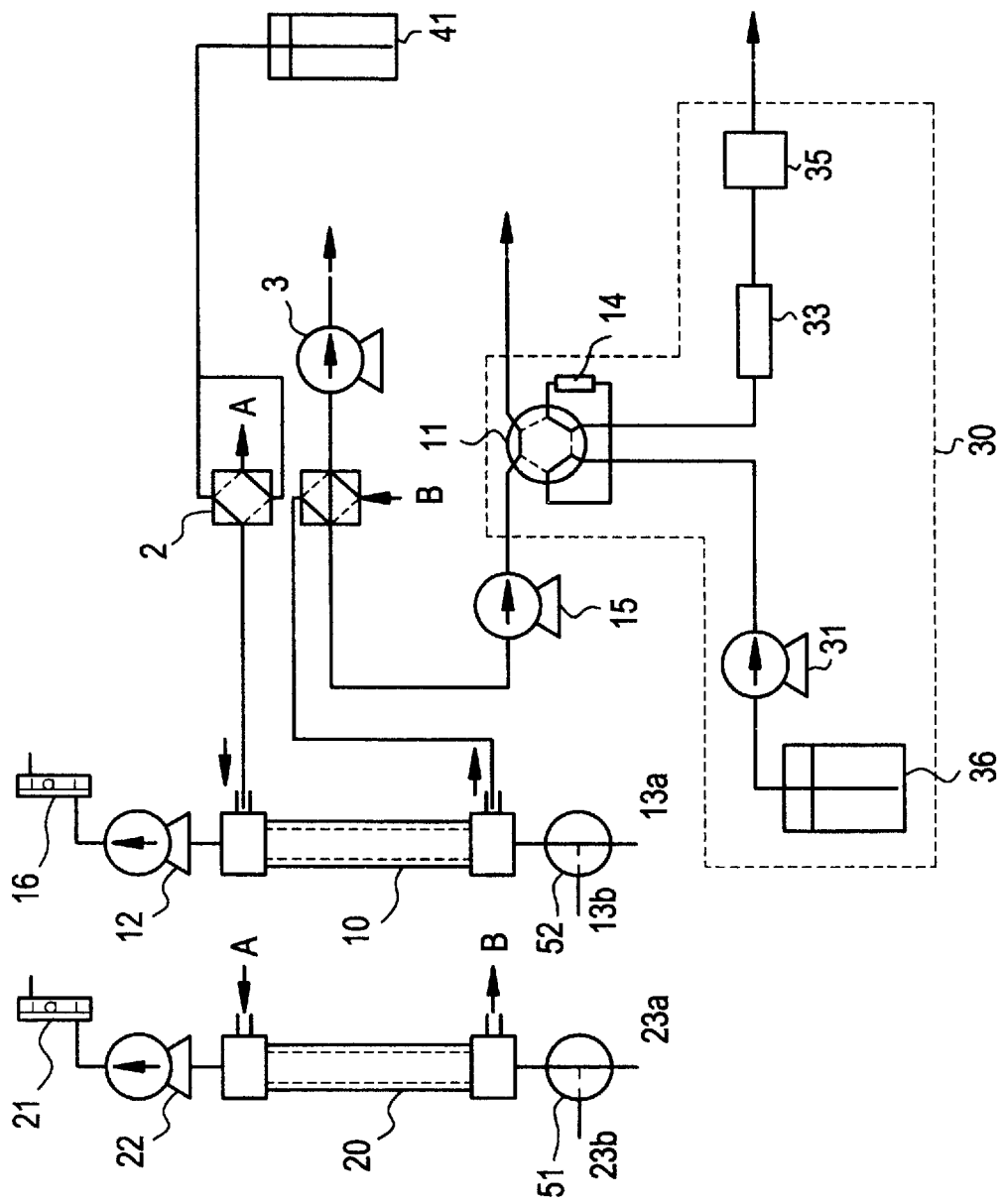
FIG. 5 outlines the total constitution of other embodiment of the present gas analyzer.
Figure 6:
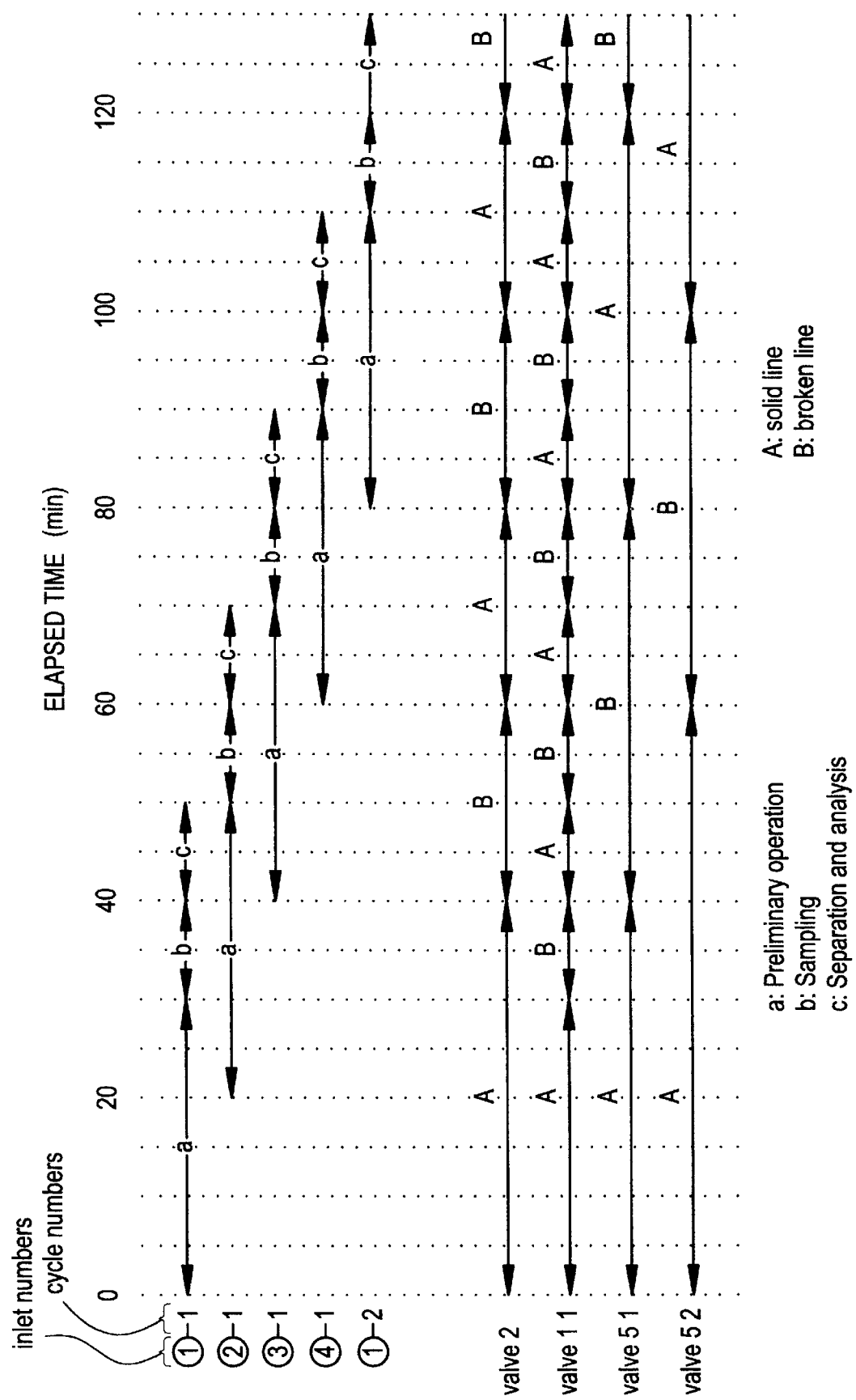
FIG. 6 shows an operational sequence of analytical steps, employed when using the gas analyzer of FIG. 5.
Figure 7:
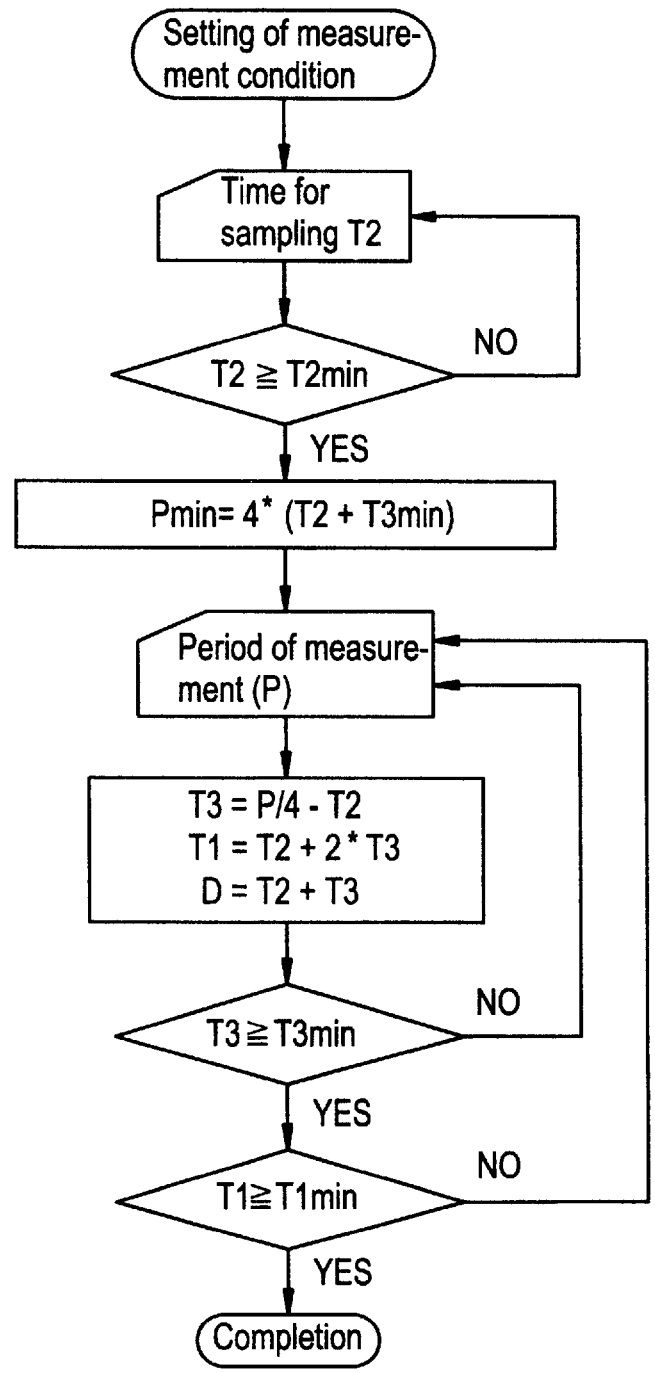
FIG. 7 is a flow chart showing a procedure for setting the measurement conditions used in conducting the operational sequence of FIG. 6.
Figure 8:
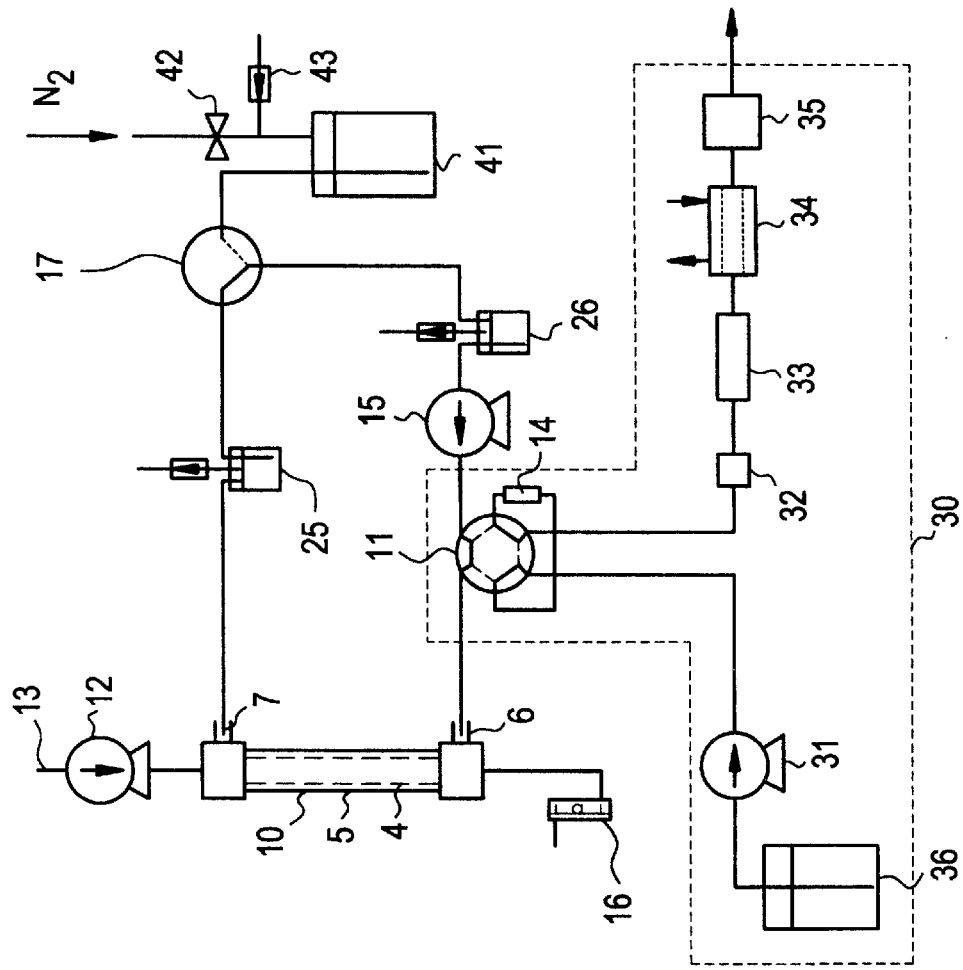
FIG. 8 outlines the total constitution of a conventional gas analyzer.

Next, the second example of the present invention is described with reference to part of the accompanying drawings. In the first example was described a gas analyzer capable of conducting measurement for two sampling points while switching them. In the present example is described a gas analyzer capable of conducting measurement for more sampling points, for example, four sampling points while switching them. FIG. 5 outlines the total constitution of the second embodiment of the present gas analyzer; FIG. 6 shows the operational sequence of analytical steps, employed when using the gas analyzer of FIG. 5; and FIG. 7 is a flow chart showing a procedure for setting the measurement conditions used in conducting the operational sequence of FIG. 6.

In FIG. 5, A and B of a diffusion scrubber body 20 are connected to A and B of a passage-switching valve 2, respectively. In FIG. 6, ①-1, ②-1, ③-1 and ④-1 are, respectively, the first measurements of gases taken into from a gas inlet 13a, a gas inlet 23a, a gas inlet 13b and a gas inlet 23b; "-2" means the second measurement and ①-2 is the second measurement of the gas taken into from the gas inlet 13a. In each measurement, a, b and c refer to a preliminary operation step, a sampling step and a separation and analysis step, respectively.

In FIG. 6, "solid line" and "broken line" of each of passage-switching valves 2, 11, 51 and 52 correspond to the switching condition of each valve in FIG. 5. The absorbing solution fed by a solution-feeding pump 15 passes through a diffusion scrubber 10 when the passage-switching valve 2 is in a solid line condition, and passes through the diffusion scrubber 20 when the passage-switching valve 2 is in a broken line condition. The absorbing solution fed by a solution-feeding pump 3 passes through another diffusion scrubber which is different from the diffusion scrubber through which the absorbing solution fed by the solution-feeding pump 15 passes.

When the passage-switching valve 11 is in a broken line condition, the solution from the diffusion scrubber is introduced into a concentration column 14, and the to-be-analyzed gas components in the solution is captured by the column 14. When the passage-switching valve 11 is in a solid line condition, preliminary operation and separation/analysis are conducted. That is, in one passage, the to-be-analyzed gas components captured by the concentration column 14 are eluted by an eluting solution sent from a storage tank 36 and fed into a separation column 33. At that time, the other passage is used for preliminary operation. Through each of the diffusion scrubber bodies 10 and 20 are always passed, from the start of their initial measurements ①-1 and ②-1, an absorbing solution and a sample gas taken from one sampling point; and the diffusion scrubber not used for sampling is always used for preliminary operation.

A time table for individual analytical steps is shown in FIG. 6. The time table for individual analytical steps is not restricted thereto and may be any as long as the sampling and separation/analysis for one sampling point and those for other sampling point are not conducted simultaneously and, with respect to each of the diffusion scrubbers, change of sampling points from one point to other is not made until sampling at one point is completed. In order to conduct continuous automatic operation, it is further necessary that the time table is set so as to satisfy the following condition:

(time for preliminary operation)≧(time for sampling+ time for separation and analysis)

Specifically, the switch of each analytical step must be conducted, as shown in FIG. 6, so that the start of the preliminary operation of ③-1 is not earlier than the start of the separation and analysis of ①-1 and that the completion of the sampling of ②-1 is not earlier than the completion of the separation and analysis of ①-1 (the same applies later). By setting the time table as shown in FIG. 6, an ion chromatograph repeats sampling and separation/analysis routinely after 30 minutes from the start of the measurement, whereby efficient measurement can be made. Incidentally, as long as the above conditions are met, the time for preliminary operation can be elongated or shortened.

In the embodiment of the present example was described a gas analyzer enabling measurements of four sampling points by switching them. A gas analyzer enabling measurements of more sampling points by switching them is made easily available by using, in place of the passage-switching valves 51 and 52, passage-switching valves each enabling the switching of three or more sampling points and also by setting an operational sequence satisfying the above-mentioned measurement conditions for analytical steps.

EXAMPLE 3

The third example of the present invention is described in detail with reference to part of the accompanying drawings. With reference to FIG. 5, description is made on a case using the same ion chromatograph, diffusion scrubbers, solution-feeding pumps and sampling pumps as in the first example, under the same conditions as in the first example. The minimum allowable time for separation and analysis (T3min) was set at 10 minutes, and the minimum allowable time for preliminary operation (T1min) was set at 20 minutes. Also, the time for sampling (T2) in the operational sequence for analytical steps, of FIG. 5 was set at 10 minutes. T2 was inputted according to the flow chart of FIG. 7; then, the minimum allowable time for period of measurement (Pmin) was calculated to be 80 minutes. This Pmin value was inputted as the period of measurement (P2); then, the time for preliminary operation (T1) became 30 minutes, the time for separation and analysis (T3) became 10 minutes, and the delay time (D) became 20 minutes. Using these set values, measurement was conducted, whereby initial analytical data for four sampling points ①, ②, ③ and ④ were obtained after 50 minutes, 70 minutes, 90 minutes and 110 minutes, respectively, from the start of measurement and, after that, analytical data were obtained every 80 minutes for each sampling point.

What is claimed is:

1. A gas parallel line analyzer used for analysis of the to-be-analyzed gas components contained in a sample gas, by absorption into an absorbing solution, which gas analyzer comprises:

two gas sampling units each comprising a tube-shaped diffusion scrubber and a sampling pump, each diffusion scrubber comprising an outer tube and an inner tube provided inside the outer tube and consisting of a gas-permeable membrane tube capable of passing therethrough only part of a sample gas, including to-be-analyzed gas components, the outer tube and the inner tube being fixed by a pair of joints at their two ends, the diffusion scrubber further comprising, at each end, a port communicating with the inner tube and a port communicating with the gap between the outer tube and the inner tube, either one of the inner tube inside and the gap between the outer tube and the inner tube being used as a passage for absorbing solution and the other being used as a passage for sample gas, and each sampling pump being connected to the passage for sample gas, of the diffusion scrubber and used for taking the sample gas into the diffusion scrubber, a solution-feeding pump for feeding an absorbing solution into the diffusion scrubber of one gas sampling unit, a solution-feeding pump for feeding the absorbing solution into the diffusion scrubber of the other gas sampling unit and introducing the solution leaving the diffusion scrubber, into a concentration column packed with an adsorbent capable of concentrating the to-be-analyzed gas components dissolved in the solution, a passage-switching valve or device for switching the first gas sampling unit connecting to the former solution-feeding pump and the second gas sampling unit connecting to the latter solution-feeding pump, to each other, so that the second gas sampling unit becomes connected to the former solution feeding pump and the first gas sampling unit becomes connected to the latter solution feeding pump, a detecting unit for detecting the to-be-analyzed gas components captured by the concentration column, and a passage-switching valve or device for switching, to each other, a passage for introducing the solution leaving the diffusion scrubber, into the concentration column for capturing and concentration of the to-be-analyzed gas components and a passage for introducing the to-be-analyzed gas components captured and concentrated by the concentration column, into the detecting unit.

2. A gas analyzer according to claim 1, wherein a passage-switching valve for switching between a plurality of gas-sampling points or locations is provided upstream of the gas inlet of each gas sampling unit.

3. A gas analyzer according to claim 1, wherein the gas-permeable membrane tube has a porosity of 40–80%, a film thickness of 0.1–0.5 mm and a water entry pressure of 0.2 kgf/cm$^2$ or more.

4. A gas analyzer according to claim 1, which carries out a gas analysis method comprising the following steps a to c, each known to require a minimum required time, in this order:

a step a of feeding, into one of the gas sampling units, an absorbing solution by the use of one solution-feeding pump and, simultaneously therewith, a sample gas containing to-be-analyzed gas components, to bring the to-be-analyzed gas components in an equilibrium state between the absorbing solution and the sample gas during a first sample cycle of gas analysis measurements, a step b of, after the step a, introducing the absorbing solution from the diffusion scrubber of the gas sampling unit into the concentration column by the use of another solution-feeding pump, and a step c of, after the step b, eluting the to-be-analyzed gas components captured by the concentration column and analyzing them by the use of the detecting unit, in which method while the step b and the step c are conducted sequentially for the sample gas taken into one gas sampling unit, the step a is conducted for the gas sample taken into the other gas sampling unit as the beginning of a next sample cycle of gas analysis measurements; as soon as the step b is completed for the sample gas taken into one gas sampling unit, the step a for the next sample cycle is started in the gas sampling unit; and this step a is completed as soon as the step c is completed for the gas sample taken into the other gas sampling unit, thereby finishing the first sample cycle of gas analysis measurements which gas analyzer has a control unit capable of automatically calculating the times for the steps a to c based on the values inputted as the minimum required times for the steps a to c and also on the value inputted as a desired period of measurement.

5. A gas analysis method using a gas analyzer of any of claims 1–3, which comprises the following steps a, b and c in this order:

a step a of feeding, into one of the gas sampling units, an absorbing solution by the use of one solution-feeding pump and, simultaneously therewith, a sample gas containing to-be-analyzed gas components, to bring the to-be-analyzed gas components in the sample gas to an equilibrium with the to-be-analyzed gas components in the absorbing solution, a step b of, after the step a, introducing the absorbing solution from the diffusion scrubber of the gas sampling unit into the concentration column by the use of another solution-feeding pump, and a step c of, after the step b, elating the to-be-analyzed gas components captured by the concentration column and analyzing them by the use of the detecting unit, in which method while the step b and the step c are conducted sequentially for the sample gas taken into one gas sampling unit, the step a is conducted for the gas sample taken into the other gas sampling unit as the beginning of a next sample cycle of gas analysis measurements.

6. A gas analysis method according to claim 5, wherein as soon as the step c is completed for the sample gas taken into one gas sampling unit, the step b is started for the sample gas taken into the other gas sampling unit.

7. A gas analysis method according to claim 5, wherein as soon as the step b is completed for the sample gas taken into one gas sampling unit, the step a for the next sample cycle is started in the other gas sampling unit and this step a is completed as soon as the step c is completed for the gas sample taken into the other gas sampling unit, thereby finishing the first sample cycle of gas analysis measurements.

* * * * *

UNITED STATES PATENT AND TRADEMARK OFFICE
CERTIFICATE OF CORRECTION

PATENT NO.: 5,841,022
DATED: November 24, 1998
INVENTOR(S): Ushio HASE

It is certified that error appears in the above-identified patent and that said Letters Patent is hereby corrected as shown below:

Column 8, Line 59  delete "parallel line" and insert --parallel line-- before "anaylsis"

Column 10, Line 39  delete "elating" and insert --eluting--

Signed and Sealed this

Twenty-second Day of June, 1999

Attest:

Attesting Officer

Q. TODD DICKINSON

Acting Commissioner of Patents and Trademarks